US012779139B2

(12) United States Patent
Stefanov et al.

(10) Patent No.: US 12,779,139 B2
(45) Date of Patent: Nov. 3, 2026

(54) INJECTION SUPPORT PAD

(71) Applicant: SHL Medical AG, Zug (CH)

(72) Inventors: Slobodan Stefanov, Deerfield Beach, FL (US); Nurettin Ali, Deerfield Beach, FL (US); Daniel Scott, Deerfield Beach, FL (US); Ramazan Gurkan Demirozer, Deerfield Beach, FL (US)

(73) Assignee: SHL Medical AG, Zug (CH)

( * ) Notice: Subject to any disclaimer, the term of this patent is extended or adjusted under 35 U.S.C. 154(b) by 374 days.

(21) Appl. No.: 18/578,214

(22) PCT Filed: Jun. 30, 2022

(86) PCT No.: PCT/EP2022/068018
§ 371 (c)(1),
(2) Date: Jan. 10, 2024

(87) PCT Pub. No.: WO2023/285151
PCT Pub. Date: Jan. 19, 2023

(65) Prior Publication Data

US 2024/0316286 A1 Sep. 26, 2024

Related U.S. Application Data

(60) Provisional application No. 63/338,812, filed on May 5, 2022, provisional application No. 63/221,508, filed on Jul. 14, 2021.

(30) Foreign Application Priority Data

Aug. 26, 2021 (EP) .................................... 21193370

(51) Int. Cl.
*A61M 5/42* (2006.01)

(52) U.S. Cl.
CPC .................................. *A61M 5/427* (2013.01)

(58) Field of Classification Search
CPC .................................................. A61M 5/3287
See application file for complete search history.

(56) References Cited

U.S. PATENT DOCUMENTS 5,137,520 A * 8/1992 Maxson ................ A61M 25/02
128/DIG. 26
5,348,543 A * 9/1994 Talley ................. A61M 5/3213
604/263

(Continued)

FOREIGN PATENT DOCUMENTS

EP 2776115 B1 3/2019
JP 3216566 A 9/1991

(Continued)

OTHER PUBLICATIONS

International Search Report and Written Opinion for corresponding PCT application No. PCT/EP2022/068018, dated Jun. 30, 2022.

(Continued)

*Primary Examiner* — David P. Olynick
(74) *Attorney, Agent, or Firm* — McDonnell Boehnen Hulbert & Berghoff LLP

(57) ABSTRACT

The present disclosure generally relates to medicament delivery devices such as autoinjectors, and particularly concerns pads for attaching medicament delivery devices such as autoinjectors to an injection site.

15 Claims, 16 Drawing Sheets

(56) References Cited

U.S. PATENT DOCUMENTS

| | | | | |
|---|---|---|---|---|
| 6,332,875 | B2 * | 12/2001 | Inkpen | A61M 5/3287 604/117 |
| 7,097,637 | B2 | 8/2006 | Triplett | |
| 7,309,326 | B2 | 12/2007 | Fangrow, Jr. | |
| 7,892,216 | B2 | 2/2011 | Fangrow, Jr. | |
| 7,896,841 | B2 | 3/2011 | Wall | |
| 8,303,545 | B2 * | 11/2012 | Schraga | A61M 5/158 604/86 |
| 8,303,574 | B2 | 11/2012 | Gray | |
| 8,313,470 | B2 * | 11/2012 | Abry | A61M 5/3202 604/198 |
| 8,915,882 | B2 * | 12/2014 | Cabiri | A61M 5/3287 604/162 |
| D784,527 | S * | 4/2017 | Llewellyn-Hyde | D24/127 |
| 9,999,725 | B2 | 6/2018 | Knobloch | |
| 10,010,675 | B2 * | 7/2018 | Cabiri | A61M 5/3202 |
| 10,105,484 | B2 | 10/2018 | Sonderegger | |
| 10,795,973 | B2 * | 10/2020 | Baker | G09B 19/0053 |
| 11,819,673 | B2 * | 11/2023 | Yudelevich | A61M 5/3205 |
| 12,154,453 | B2 * | 11/2024 | Baker | A61M 5/31528 |
| 12,518,655 | B2 * | 1/2026 | Baker | A61M 5/20 |
| 2001/0044606 | A1 * | 11/2001 | Inkpen | A61M 5/3287 604/181 |
| 2002/0055711 | A1 * | 5/2002 | Lavi | A61M 5/326 604/110 |
| 2003/0229308 | A1 * | 12/2003 | Tsals | A61M 5/20 604/116 |
| 2004/0138629 | A1 * | 7/2004 | Cipoletti | A61M 5/3275 604/263 |
| 2007/0276320 | A1 | 11/2007 | Wall et al. | |
| 2010/0030155 | A1 * | 2/2010 | Gyrn | A61M 25/0612 604/164.08 |
| 2011/0040280 | A1 * | 2/2011 | Iljitsu | A61M 5/3287 604/506 |
| 2013/0116624 | A1 * | 5/2013 | Plunnecke | A61M 5/008 604/187 |
| 2013/0218090 | A1 * | 8/2013 | Roberts | A61M 5/3271 604/192 |
| 2014/0163526 | A1 | 6/2014 | Cabiri et al. | |
| 2014/0324021 | A1 | 10/2014 | Ulrich | |
| 2016/0106930 | A1 * | 4/2016 | Bitar | A61M 5/2033 604/115 |
| 2016/0235915 | A1 * | 8/2016 | Cabiri | A61M 5/3287 |
| 2016/0367766 | A1 * | 12/2016 | Baker | A61M 5/3287 |
| 2017/0173270 | A1 * | 6/2017 | Nakamura | A61M 5/3204 |
| 2017/0274158 | A1 * | 9/2017 | Saeed Malik | A61M 5/3287 |
| 2019/0030240 | A1 * | 1/2019 | Cabiri | A61M 5/14248 |
| 2019/0160226 | A1 | 5/2019 | Chaves, Sr. | |
| 2019/0160230 | A1 * | 5/2019 | Yudelevich | A61M 5/3232 |
| 2020/0197622 | A1 * | 6/2020 | McLusky | A61M 5/3287 |
| 2020/0206438 | A1 * | 7/2020 | Baker | A61M 5/425 |
| 2021/0090466 | A1 | 3/2021 | Baker | |
| 2021/0128844 | A1 | 5/2021 | Boyaval | |
| 2021/0268188 | A1 * | 9/2021 | Katuin | A61M 5/31576 |
| 2021/0361883 | A1 * | 11/2021 | Yudelevich | A61M 5/3232 |
| 2023/0146367 | A1 * | 5/2023 | Dasbach | A61M 5/422 604/112 |
| 2023/0381426 | A1 * | 11/2023 | Pedersen | A61M 5/20 |

FOREIGN PATENT DOCUMENTS

| | | | |
|---|---|---|---|
| JP | 3223479 | A | 10/2001 |
| JP | 5905968 | B2 | 4/2016 |
| JP | 2018-532528 | A | 11/2018 |
| JP | 3230183 | U | 1/2021 |

OTHER PUBLICATIONS

Notice of Reasons for Rejection issued by the Japanese Patent Office in application No. 2024-501894 dated Dec. 12, 2024.

* cited by examiner

INJECTION SUPPORT PAD

CROSS REFERENCE TO RELATED APPLICATIONS

The present application is a U.S. National Phase Application pursuant to 35 U.S.C. § 371 of International Application No. PCT/EP2022/068018 filed Jun. 20, 2022, which claims priority to (i) U.S. Provisional Patent Application No. 63/221,508 filed Jul. 14, 2021, (ii) European Patent Application No. 21193370.0 filed Aug. 26, 2021, and (iii) U.S. Provisional Patent Application No. 63/338,812 filed May 5, 2022. The entire disclosure contents of these applications are herewith incorporated by reference into the present application.

TECHNICAL FIELD

The present disclosure generally relates to medicament delivery devices such as autoinjectors, and particularly concerns pads for attaching medicament delivery devices such as autoinjectors to an injection site.

BACKGROUND

A number of medical conditions require injections. These days, a number of different injection devices exist, including various types of pen injectors, autoinjectors and on-body devices. Although many of these devices have enabled major improvements in the management of a number of medical conditions, various limitations do still exist in the current technology. Not least amongst these are the difficulties faced by patients that require frequent injections and by patients that need to inject particularly viscous drugs. In considering these problems, the applicant has appreciated that various developments could be made to help improve the medicament delivery devices on the market today, which are set out in more detail below.

SUMMARY

An object of the present disclosure is to provide a pad which solves, or at least mitigates problems of the prior art.

According to a first aspect of the present discloses, there is provided a pad extending along an axis from a proximal end to a distal end. The proximal end is the end of the pad adjacent to an injection site when the pad is in use. The pad comprises an attachment portion configured to receive a medicament delivery device, and a support structure at the proximal end of the attachment portion configured to abut against the medicament delivery device when in use and the medicament delivery device is arranged in the attachment portion. The support structure is configured to be pushed away from the attachment portion by a force exerted by a cover extension of the medicament delivery device when transitioning from a retracted position to an extended position, such that the cover extension is allowed to move to the extended position in response to the pad being removed from the injection site while the medicament delivery device is present in the attachment portion.

Embodiments of the present disclosure provides for advantageous pads that, when in use, are attached at an injection site. The pad has an attachment portion that, when in use, locks a medicament delivery device in place, until a user disengages the medicament delivery device. It is desirable that a medicament delivery member, such as a needle, is not exposed if the user removes the pad from the injection site before the medicament delivery device is disengaged from the attachment portion. To address this, the embodiments of the present disclosure provide means for ensuring that the cover extension is transitioned to the extended position, protecting the needle, in case the pad is removed from the injection site prior to disengaging the medicament delivery device from the attachment portion.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the components thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal" and "transversally" refer to a direction generally perpendicular to the longitudinal direction.

Further, the terms "circumference", "circumferential", "circumferentially" refer to a circumference or a circumferential direction relative to an axis, typically a central axis extending in the direction of the longest extension of the device and/or component. Similarly, "radial" or "radially" refer to a direction extending radially relative to the axis, and "rotation", "rotational" and "rotationally" refer to rotation relative to the axis.

The same direction terminology has been used to describe other components such as the pad—for example, the proximal end of the pad is the part of the pad closest to the dose delivery site (injection site), and the distal end of the pad is the part of the pad furthest from the dose delivery site. In the Figures, the longitudinal direction is the direction of axis 102, with the corresponding circumferential direction 31 and radial direction 32 relative to the axis 102 also shown.

When the wording 'at the injection site' or 'at the dose delivery site' is used in this application, it generally refers to the point where the medicament delivery device (e.g. a needle) enters the patient, along with the surrounding area, for example the area where the pad is attached.

According to one embodiment, the support structure may be at the proximal end of the pad adjacent to the injection site when the pad is in use.

According to one embodiment, the support structure may be configured to allow the cover extension to penetrate through the attachment portion to beyond a plane of the proximal end of the pad. Thus, the support structure is advantageously configured so that the cover extension, when transitioning to the extended position, pushes the support structure and penetrates through the pad.

According to one embodiment, the support structure may comprise at least one flexible arm attached to the pad, the at least one flexible arm being configured to flex by the force from the cover extension. The flexible arm may be resiliently flexible, i.e. flexing back towards the original position after use. When the pad is attached at the injection site with the medicament delivery device in the attachment portion, the flexible arms are maintained in their original position by the counterforce provided by the user's body surface at the injection site.

Once the pad is removed, the at least one flexible arm is advantageously pushed in the proximal direction by the force from the cover extension transitioning to the extended position. The at least one flexible arm provides a relatively simple yet reliable way of ensuring that the cover extension is transitioned to the extended position, protecting the needle, in case the pad is removed from the injection site prior to disengaging the medicament delivery device from the attachment portion.

According to one embodiment, the support structure may comprise a proximal injection surface configured to be separated from the attachment portion by the force exerted by the cover extension. This separable support structure provides another advantageous configuration of the support structure. In one example embodiment, the proximal injection surface may be hinged to a side structure of the pad. This provides for maintaining the support structure connected to the pad after use and to be returned to its original position after use. The hinge may for example be a living hinge.

According to one embodiment, the proximal injection surface may comprise a clip configured to hold the support structure including the proximal injection surface in place prior to release by the force exerted by the cover extension. This provides for ensuring that the proximal injection surface is in a correct position prior to using the pad. Further, the clip is advantageously configured to hold the proximal injection surface in place with a force that is adapted such that it is overcome by the cover extension pushing on the support structure while the medicament delivery device is attached in the attachment portion when the pad is removed from the injection site.

According to one embodiment, the proximal injection surface may be adjacent to the injection site when the pad is in use.

According to one embodiment, the proximal injection surface may extend across at least half the area of the proximal end of the pad.

According to one embodiment, the support structure may comprise a set of clips configured to releasably lock the support structure to the attachment portion, wherein the set of clips are releasable by the cover extension when inserted in the attachment portion. This is yet another advantageous configuration of the support structure which is provided with clips that lock the support structure to the attachment portion. Thus, the support structure is releasable from the attachment portion. The clips are configured so that the force exerted on them by the housing of the medicament delivery device when it is engaged in the attachment portion, puts the clips in a release position where the support structure is releasable from the attachment portion.

In one example embodiment, the clips may comprise a flexible arm with a protrusion extending through a through-hole of a wall of the attachment portion, wherein the protrusion is configured to be pushed out from the through-hole by the cover extension to thereby release the support structure from the attachment portion. In one example embodiment, the flexible arms may be substantially parallel with the wall of the attachment portion.

According to one embodiment, the proximal injection surface may comprise an adhesive. The adhesive provides for attaching the pad to the injection site.

There is according to a second aspect of the present disclosure provided a pad extending along an axis from a proximal end to a distal end. The proximal end is the end of the pad adjacent to an injection site when the pad is in use. The pad comprises an attachment portion configured to releasably receive a medicament delivery device. The attachment portion comprises a release mechanism which, upon being actuated, releases the medicament delivery device from the pad, and a release arm configured to act on the release mechanism when the pad is being removed from the injection site by transferring a force from the pad caused by the pad being deformed while being removed from the injection site to the release mechanism.

This aspect provides similar advantages as the ones discussed above with regards to the first aspect.

According to one embodiment, the release arm may be attached to a pad surface at the distal end of the pad and extends to a distal surface of a release button of the release mechanism, wherein when the release arm acts on the distal surface of the release button, the release mechanism is actuated. In one example embodiment, the release arm acts to push the release button towards a surface at the distal end of the pad, thus the release arm pushes the release button in a proximal direction. The release arm may be hook shaped to act on a distal surface of the release button. In one example, the release button may be attached to the surface at the distal end of the pad via a linkage arm.

According to one embodiment, the release arm may be attached to a removing tab of the pad adapted to be pulled by the user for removing the pad from the injection site. Thus, when the user pulls the removing tab intended for removing the pad from the injection site, the release arm is advantageously caused to actuate the release mechanism, thereby providing for timely transfer of the cover extension to the extended position.

According to one embodiment, a first end of the release arm may be attached to a proximal surface of a release button of the release mechanism, and a second end of the release arm may be adapted to abut against a distal surface of the pad, whereby when the pad is removed from the injection site the release arm flexes such that the second end moves in a direction towards the distal end of the pad whereby the release button is spatially transferred to cause the actuation of the release mechanism.

According to one embodiment, the release arm may comprise a first arm portion and a second arm portion forming an acute angle between them, the first arm portion comprising the first end and the second arm portion comprising the second end, wherein the joint between the first and second arm portions abut against a stop edge of the pad to prevent the joint from moving towards the attachment portion, whereby when the release arm flexes the angle between the first arm portion and the second arm portion increases thereby causing the release button to move away from the attachment portion and thereby actuate the release mechanism.

In one embodiment, the attachment portion may comprise a friction lock.

Generally, all terms used in the claims are to be interpreted according to their ordinary meaning in the technical field, unless explicitly defined otherwise herein. All references to "a/an/the member, apparatus, component, means, etc." are to be interpreted openly as referring to at least one instance of the member, apparatus, component, means, etc., unless explicitly stated otherwise.

BRIEF DESCRIPTION OF THE DRAWINGS

The specific embodiments of the presently disclosed concept will now be described, by way of example, with reference to the accompanying drawings, in which.

DETAILED DESCRIPTION

The presently disclosed concept will now be described more fully hereinafter with reference to the accompanying drawings, in which exemplifying embodiments are shown. The presently disclosed concept may, however, be embodied in many different forms and should not be construed as limited to the embodiments set forth herein; rather, these embodiments are provided by way of example so that this disclosure will be thorough and complete, and will fully convey the scope of the presently disclosed concept to those skilled in the art. Like numbers refer to like members throughout the description.

Figure 1:
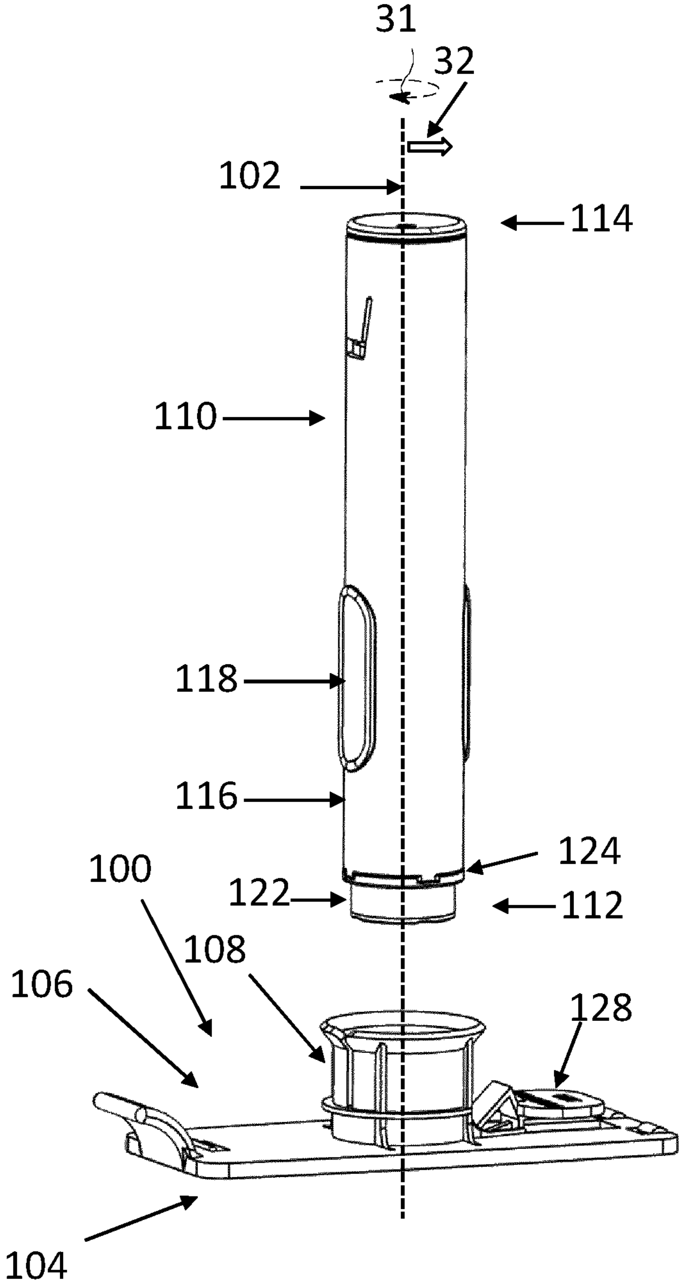
FIG. 1 is a perspective view of a pad and an autoinjector according to embodiments of the present disclosure.
Figure 2:
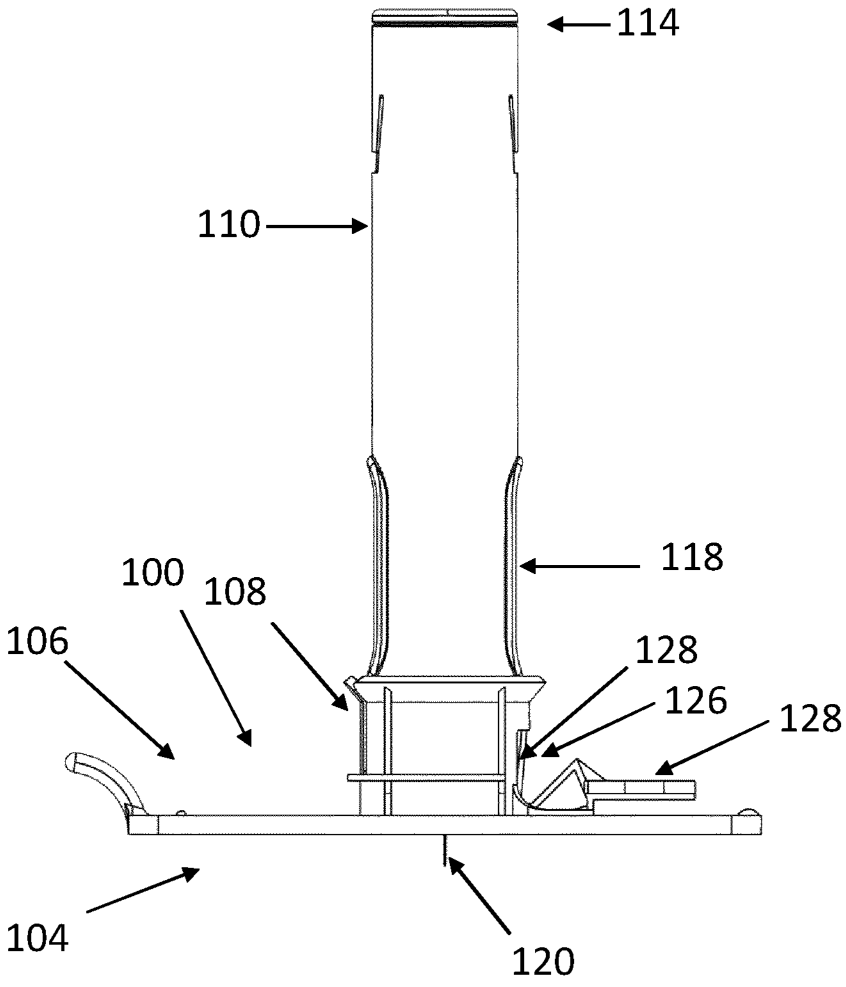
FIG. 2 is a side view of the pad and autoinjector in FIG. 1.

FIGS. 1 and 2 show an example of a pad 100 according to embodiments of the present disclosure. The pad 100 extends along an axis 102 from a proximal end 104 to a distal end 106. The proximal end 104 is the end of the pad adjacent to an injection site when the pad is in use. The injection site is understood as the drug delivery site.

The pad 100 comprises an attachment portion 108 configured to receive a medicament delivery device 110, such as an autoinjector or pen injector.

The medicament delivery device 110 in FIGS. 1 and 2 extends from a proximal end 112 to a distal end 114 relative to the axis 102. The medicament delivery device 110 comprises a housing 116, a window 118, a needle 120, and a cover extension 122 configured to cover the needle 120. The medicament delivery device 110 also comprises an attachment portion 124, which is configured to engage with the attachment portion 108 of the pad 100.

The attachment portion 108 of the pad 100 is equipped with a locking mechanism 126 for releasably locking the medicament delivery device 110 to the pad 100. The locking mechanism 126 may be configured in various ways, for example as a friction lock where a movable arm 127 applies a holding force on the attachment portion 124 of the medicament delivery device 110, or a snap-fit lock, where a protrusion on the proximal end of the housing 116 of the medicament delivery device 110 engages with a corresponding part on the attachment portion 108 of the pad 100, locking the medicament delivery device 110 into place.

Further, the pad 100 optionally comprises a release button 128 configured such that actuating the release button 128 releases the medicament delivery device from the attachment portion 108.

FIG. 2 illustrates the medicament delivery device 110 attached to the pad 100 at the attachment portion 108. The needle 120 extends out from the proximal end 104 of the pad 100. In this state, the cover extension, sometimes referred to as a needle guard, is in a retracted position, thereby exposing the needle 120. It is desirable that the needle 120 is not maintained in this exposed state if the pad 100 is removed from the injection site with the medicament delivery device 110 attached in the attachment portion 108.

For addressing the problem of the exposed needle, the pad 100 is provided with a support structure which may be provided in various configurations which will now be described in more detail.

Figure 3:
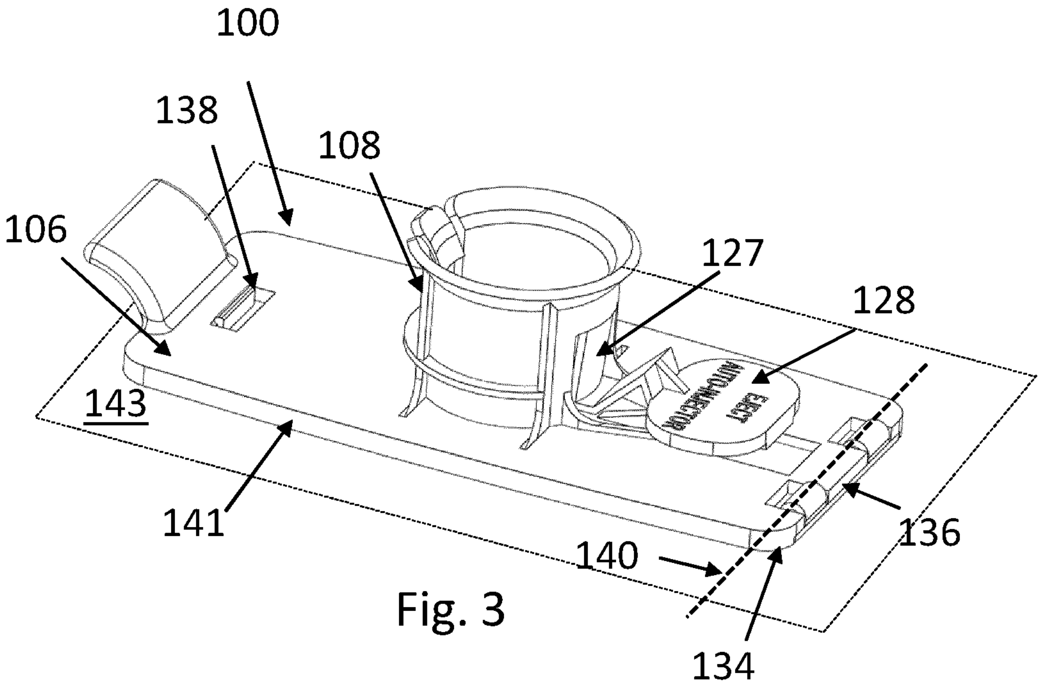
FIG. 3 is a perspective view of the pad in FIGS. 1 and 2.
Figure 4:
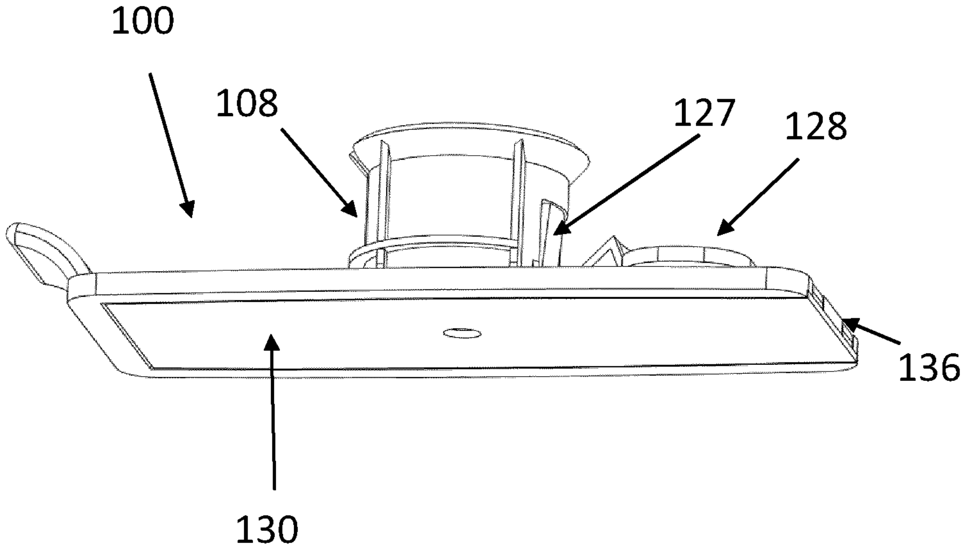
FIG. 4 is a perspective view of the pad in FIGS. 1 and 2.

Turning now to FIGS. 3 and 4 showing two perspective views of the pad 100. The pad 100 comprises a support structure 130 at the proximal end of the attachment portion 108. The support structure 130 is configured to abut against the medicament delivery device when in use and the medicament delivery device is arranged in the attachment portion 108. The support structure 130 provides a distal support surface in the attachment portion 108. The distal support surface faces in the distal direction and is located at the proximal end of the attachment portion 108.

Figure 5:
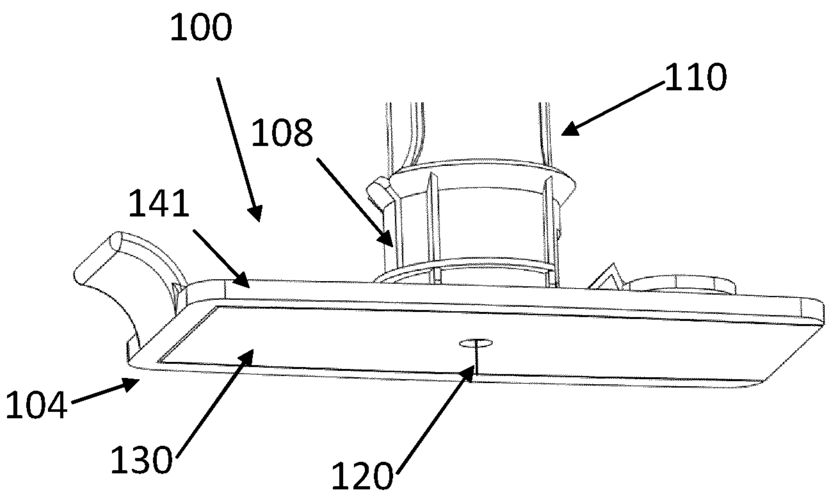
FIG. 5 is a perspective view of a pad and an autoinjector with the cover extension in a retracted position, according to embodiments of the present disclosure.

FIG. 5 illustrates the pad 100 with the medicament delivery device 110 attached to the pad 100 in the attachment portion 108 with the needle 120 extending out at the proximal end 104 of the pad 100. In this state, the cover extension 122 is in a retracted position. Generally, the cover extension is biased, e.g. by a spring, towards the extended position where it protects the needle 120.

Figure 6:
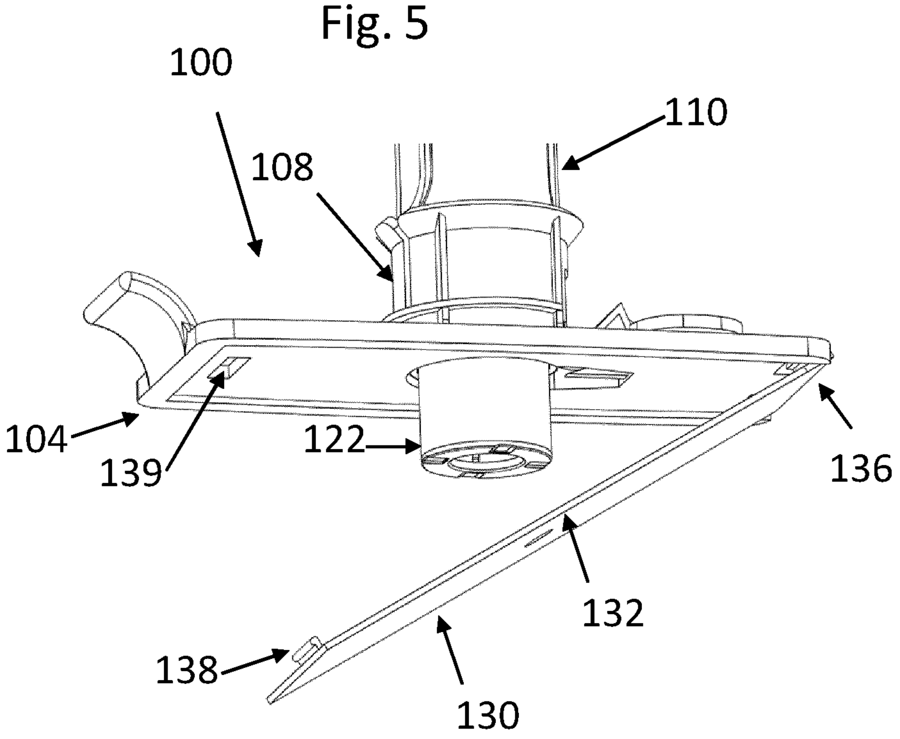
FIG. 6 is a perspective view of the pad and the autoinjector in FIG. 5 with the support structure pushed away from the attachment portion.

As illustrated in FIG. 6, the support structure 130 is configured to be pushed away from the attachment portion 108 by a force exerted by the cover extension 122 of the medicament delivery device 110 when transitioning from a retracted position to an extended position, such that the cover extension 122 is allowed to move to the extended position in response to the pad 100 being removed from the injection site while the medicament delivery device 110 is present in the attachment portion 108.

The support structure 130 is at the proximal end of the pad 100 adjacent to the injection site when the pad is in use. Further, the support structure 130 is configured to allow the cover extension 122 to penetrate through the attachment portion 108 to beyond a plane of the proximal end 104 of the pad 100. Thus, the cover extension 122 reaches to the proximal end of the pad 100 when the support structure 133 has been removed from the proximal end 104.

The support structure 130 is in this present embodiment a plate-shaped structure generally parallel with the body 141 of the pad 100. The support structure 130 comprises a proximal injection surface 132 configured to be separated from the attachment portion 108 by the force exerted by the spring biased cover extension 122. The proximal injection surface 132 is the surface being attached to the injection site via e.g. an adhesive. Thus, the proximal injection surface 132 is adjacent to the injection site when the pad is in use. Here, the proximal injection surface extends across the substantially the entire proximal end 104 of the pad 100.

In this embodiment, the support structure 130 including the proximal injection surface 132 is hinged to a side structure 134 of the pad 100. Thus, the pad 100 comprises a hinge 136 connecting the planar support structure 130 to the body of the pad 100.

On an opposite side of the hinge 136 the support structure 130 including the proximal injection surface 132 comprises a clip 138 configured to hold the proximal injection surface 132 in place prior to release by the force exerted by the cover extension 122. The clip 138 is arranged on a distal side of the support structure and is configured to lock in a receiving slot 139 of the body 141 of the pad 100.

When the support structure 130 is released at the clip-slot connection, the support structure 130 rotates about an axis 140, best seen in FIG. 3, parallel to a main plane 143 of the body 141 of the pad 100 so that the attachment portion 108 forms a through-hole through which the cover extension 122 can extend.

As long as the pad 100 is attached to the injection site, the counter force maintains the support structure 130 in place. However, if the pad 100 is removed from the injection site with the medicament delivery device 110 locked in the attachment portion 108, the counterforce no longer applies, whereby the force from the cover extension releases the clip 138 and the support structure 130 swings open at the hinge 136. Consequently, the cover extension 122 is transitioned to a retracted state in which the needle 120 is covered.

Figure 7:
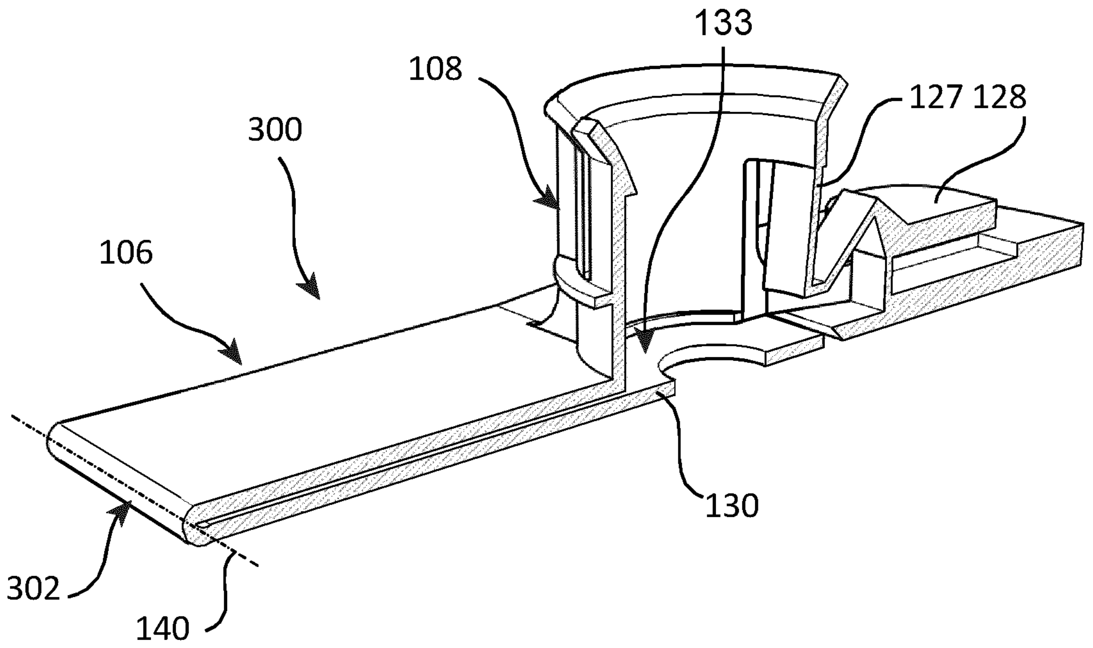
FIG. 7 is a perspective cross-sectional view of a pad according to embodiments of the present disclosure.
Figure 8A:
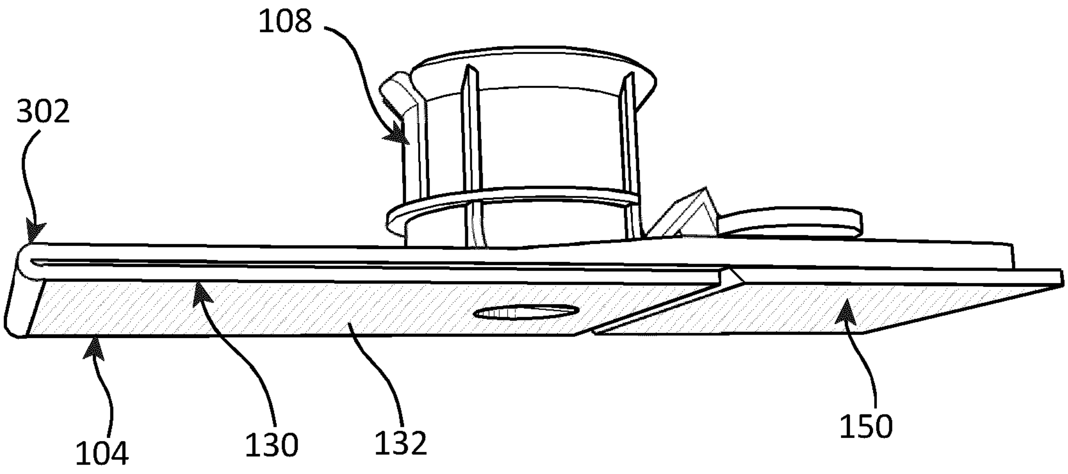
FIG. 8A is a perspective cross-sectional view of a pad according to embodiments of the present disclosure.
Figure 8B:
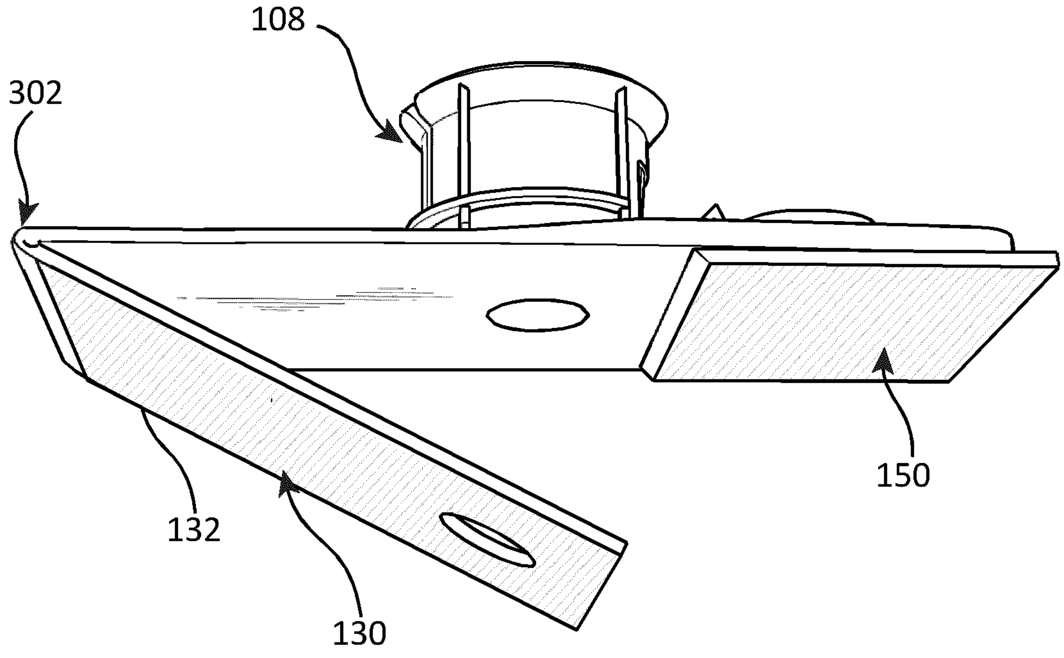
FIG. 8B is a perspective cross-sectional view of the pad in FIGS. 7 and 8A, with the support structure pushed away from the attachment portion.
Figure 9:
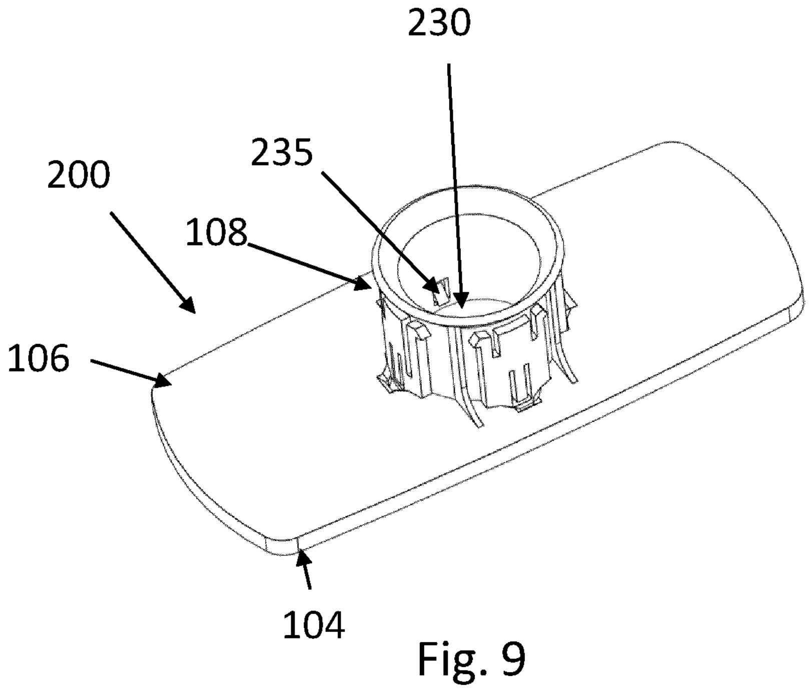
FIG. 9 is a perspective cross-sectional view of a pad according to embodiments of the present disclosure.

FIGS. 7 and 8A-B illustrate an embodiment of a pad 300 sharing similar components to the pad 100, with a difference that the hinge is a living hinge 302. Similar to the function of the pad 100, when the cover extension 122 pushes on the distal support surface 133 at the proximal end of the attachment portion 108, the living hinge 302 swings open and support structure 130 including the proximal injection surface 132 folds away from the attachment portion 108, best seen in FIG. 8B. The living hinge 302 provides for the support structure 130 including the proximal injection surface 132 to rotate across the axis 140 as discussed also in relation to FIG. 3.

As better seen in FIGS. 8A-B, the proximal end 104 comprises the foldable support structure 130 and a non-foldable portion 150 that ensures that the proximal end 104 can lay flat on the injection site. The proximal injection surface 132 of the support structure 130 here extends across at least half the area of the proximal end 104 of the pad 300.

FIGS. 9-13 illustrate another embodiment of the present disclosure. The pad shares similar components to the pad 100 illustrated in FIGS. 1-8. For example, the pad 200 pad extends along an axis 102 from a proximal end 104 to a distal end 106. The proximal end 104 is the end of the pad adjacent to an injection site when the pad is in use. The injection site is understood as the drug delivery site.

The pad 200 comprises an attachment portion 108 configured to receive a medicament delivery device 110, such as an autoinjector or pen injector. The medicament delivery device 110 and possible attachment means in the attachment portion 108 are described above and will not be repeated here.

The pad 200 comprises a support structure 230 according to an embodiment of the present disclosure. The support structure 230 is at the proximal end 104 of the pad 200 adjacent to the injection site when the pad 200 is in use.

The support structure 230 is configured to abut against the medicament delivery device 110 when in use and the medicament delivery device 110 is arranged in the attachment portion 108. The support structure 230 provides a distal support surface 233 in the attachment portion 108. The distal support surface 233 faces in the distal directing of the pad 200.

Figure 10:
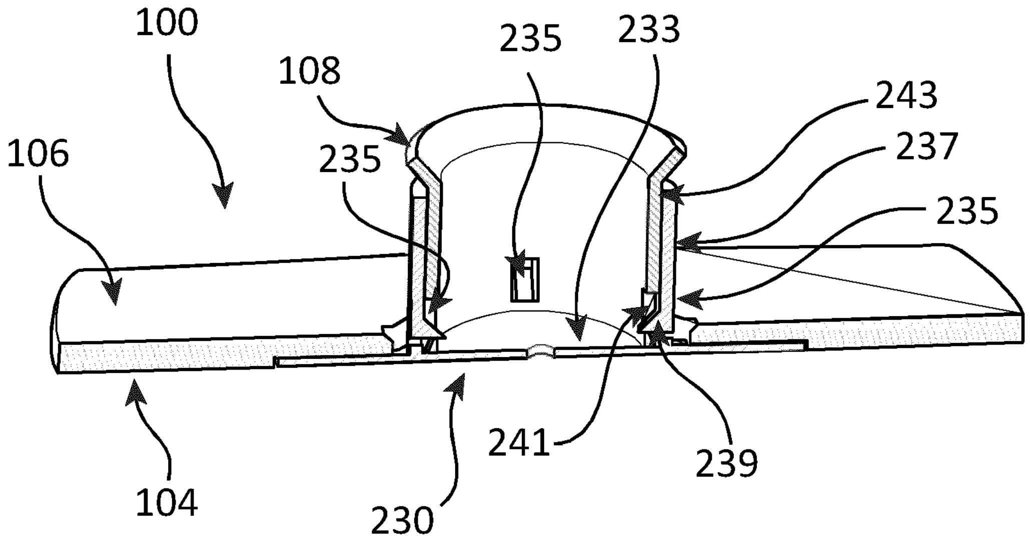
FIG. 10 is a perspective cross-sectional view of the pad in FIG. 9.

Turning to FIG. 10, illustrating a cross-sectional view of the pad 200, the support structure 230 comprises a set of clips 235 configured to releasably lock the support structure 230 to the attachment portion 108. The clips 235 are actuated to a releasable state by the medicament delivery device 110 when inserted in the attachment portion. The clips 235 when engaged with the attachment portion 108 maintain the support structure 230 in place to provide distal support surface 233 at the proximal end of the attachment portion 108.

When the medicament delivery device 110 is engaged in the attachment portion 108, the proximal end 112 of the medicament delivery device 110 acts on the clips 235 so that they are disengaged from the attachment portion 108, thereby releasing the support structure 230.

However, as long as a counter force is provided from the injection site, the support structure 230 is maintained in position.

Figure 11:
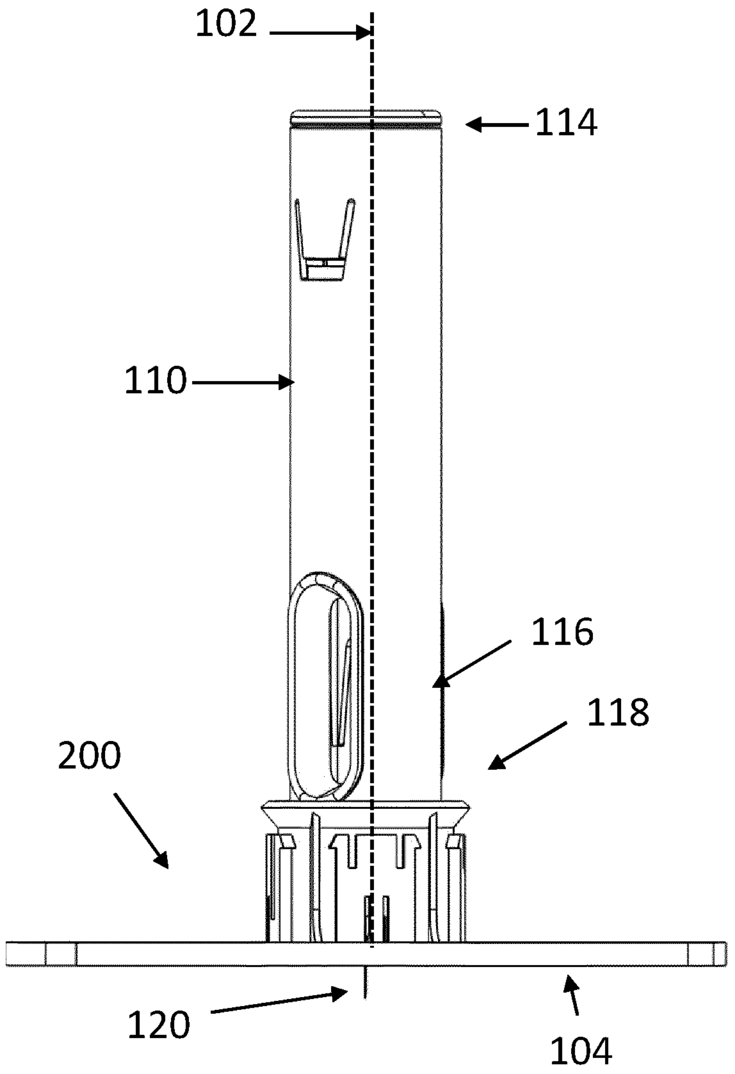
FIG. 11 is a side view of the pad in FIG. 10 and an autoinjector.
Figure 12:
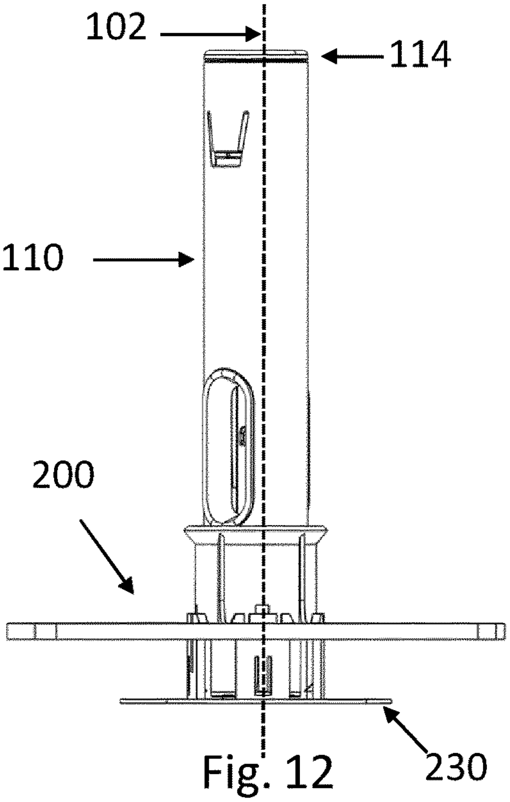
FIG. 12 is a is a side view of the pad and autoinjector in FIG. 11 with the support structure pushed away from the attachment portion.

FIG. 11 illustrates the pad 200 with the medicament delivery device 110 in place in the attachment portion 108 with the needle extending out at the proximal end 104. Thus, the cover extension of the medicament delivery device 110 is in a retracted position. The support structure 230 is configured to be pushed away from the attachment portion 108 by a force exerted by the cover extension 122 of the medicament delivery device 110, as shown in FIGS. 12 and 13, when transitioning from a retracted position to an extended position, such that the cover extension 122 is allowed to move to the extended position in response to the pad 200 being removed from the injection site while the medicament delivery device 110 is present in the attachment portion 108.

Turning again to FIG. 10, the clips 235 each comprise a flexible arm 237 with a protrusion 239 radially extending through a through-hole 241 of a wall 243 of the attachment portion 108. The protrusion 239 is configured to be pushed radially out from the through-hole 241 by the medicament delivery device 110 to thereby release the support structure 230 from the attachment portion 108. The flexible arms (only one is numbered) are substantially parallel with the wall 243 of the attachment portion 108.

Figure 13:
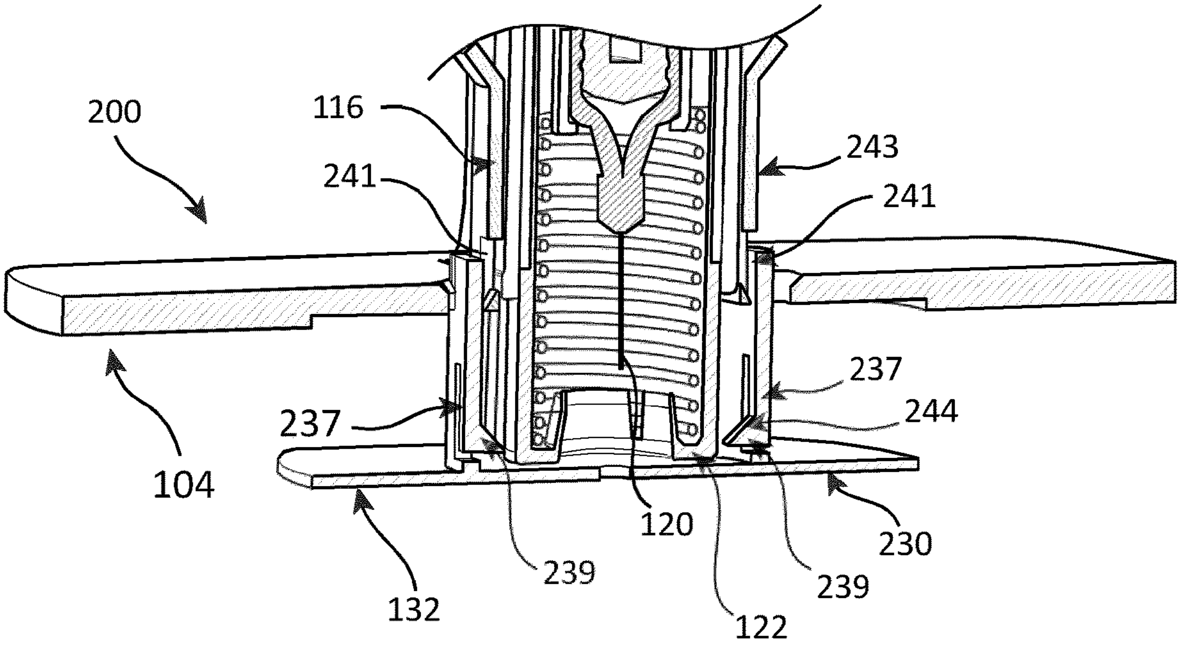
FIG. 13 is a perspective cross-sectional view of the pad and part of the autoinjector in FIG. 12.

FIG. 13 is a perspective cross-section of the pad 200 when the cover extension 122 has pushed the released support structure 230 away from the attachment portion 108. In this position, the support structure 230 is configured to allow the cover extension 122 to penetrate through the attachment portion 108 to beyond a plane of the proximal end 104 of the pad 200.

The support structure 230 comprises a proximal injection surface 132 and is configured to be separated from the attachment portion 108 by the force exerted by the spring biased cover extension 122. The proximal injection surface 132 is the surface being attached to the injection site via e.g. an adhesive. Thus, the proximal injection surface 132 is adjacent to the injection site when the pad is in use. Here, the proximal injection surface 132 extends across the only part of the entire proximal end 104 of the pad 100.

In the initial state, shown in FIG. 11, the housing 116 pushes on the protrusions 239, see FIG. 10 or 13, so that the flexible arms 237 are resiliently radially pushed out from the respective through-hole 241. The protrusions comprise an inclined surface 244 adapted for the housing 116 to slide against for causing the protrusions 239 to be forced radially out from the engaged position in the through-hole 241.

Figure 14:
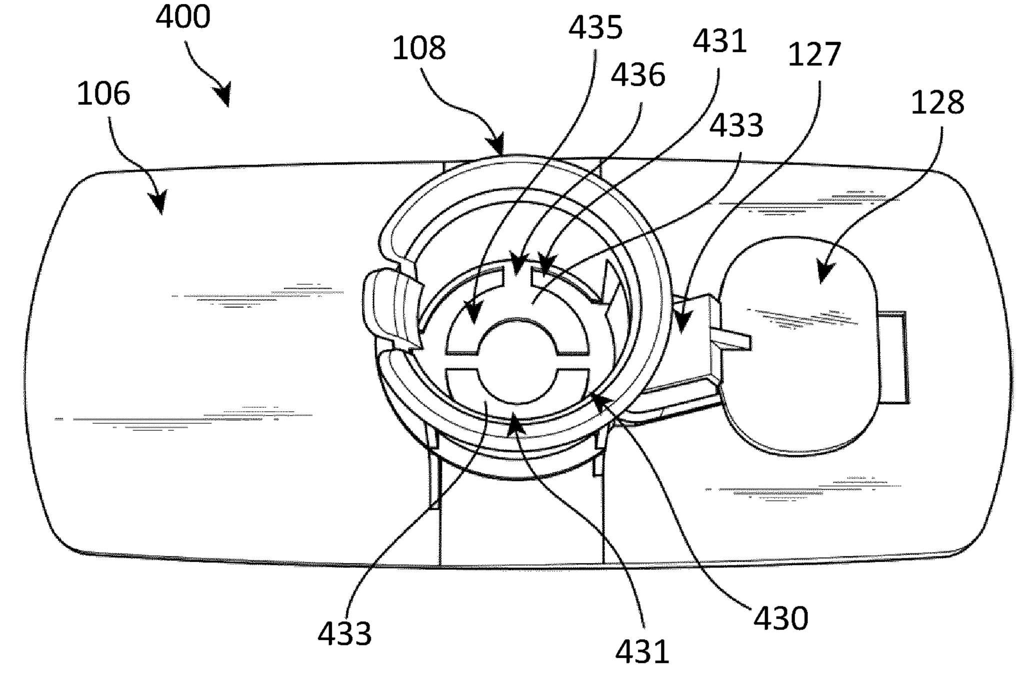
FIG. 14 is a perspective distal view of a pad according to embodiments of the present disclosure.
Figure 15:
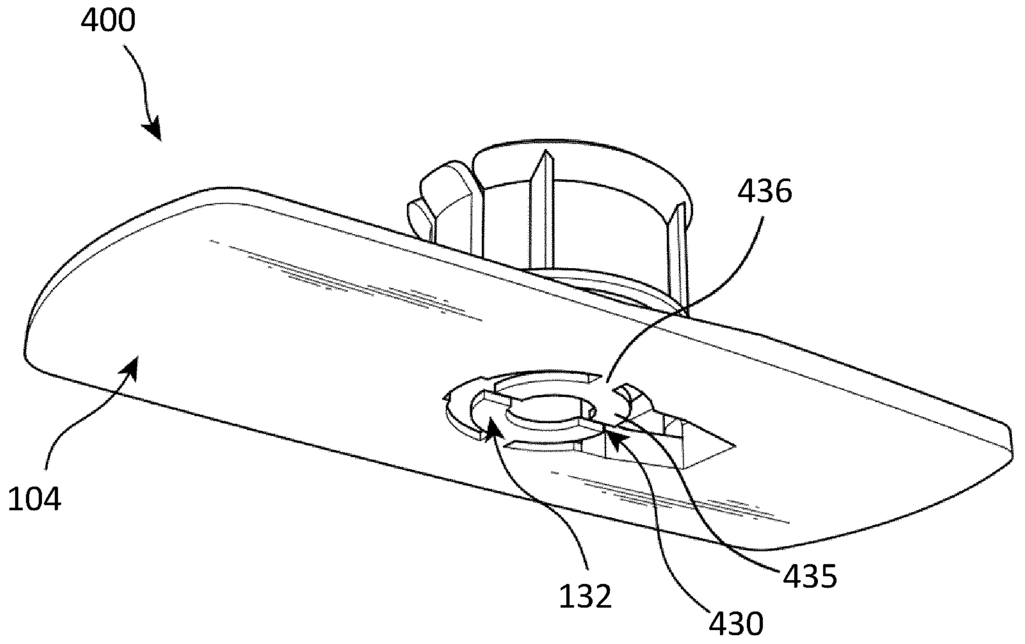
FIG. 15 is a perspective proximal view of the pad in FIG. 14.

FIGS. 14 and 15 illustrate a pad 400 according to another embodiment. The pad 400 comprises similar components to the embodiments described with reference to preceding drawings and are numbered with the same reference numerals, and that will not be repeated here.

However, the pad 400 comprises a support structure 430 that differs from those of the other embodiments. The support structure 430 is provided in the form of flexible arms 431 attached to the pad 400. The flexible arms 431 provide a distal support surface 433 for the medicament delivery device when it is engaged in the attachment portion 108. The flexible arms 431 are configured to be pushed away from the attachment portion 108 by the force exerted by the cover extension of the medicament delivery device when transitioning from a retracted position to an extended position, such that the cover extension is allowed to move to the extended position in response to the pad 400 being removed from the injection site while the medicament delivery device is present in the attachment portion 108. In other words, the at least one flexible arm 431 is configured to flex by the force from the cover extension. The flexible arms 431 are configured such that when the pad 400 is removed from the injection site, the force from the spring-biased cover extension is sufficient for flexing the flexible arms such that the cover extension can penetrate through the attachment portion in the proximal direction to beyond a plane of the proximal end of the pad 400.

In this particular embodiment shown in FIGS. 14 and 15, the flexible arms 431 each comprise a U-shaped structure 435 and a linkage arm 436 connecting the U-shaped structure 435 with the attachment portion 108 at the proximal end 104.

Figure 16:
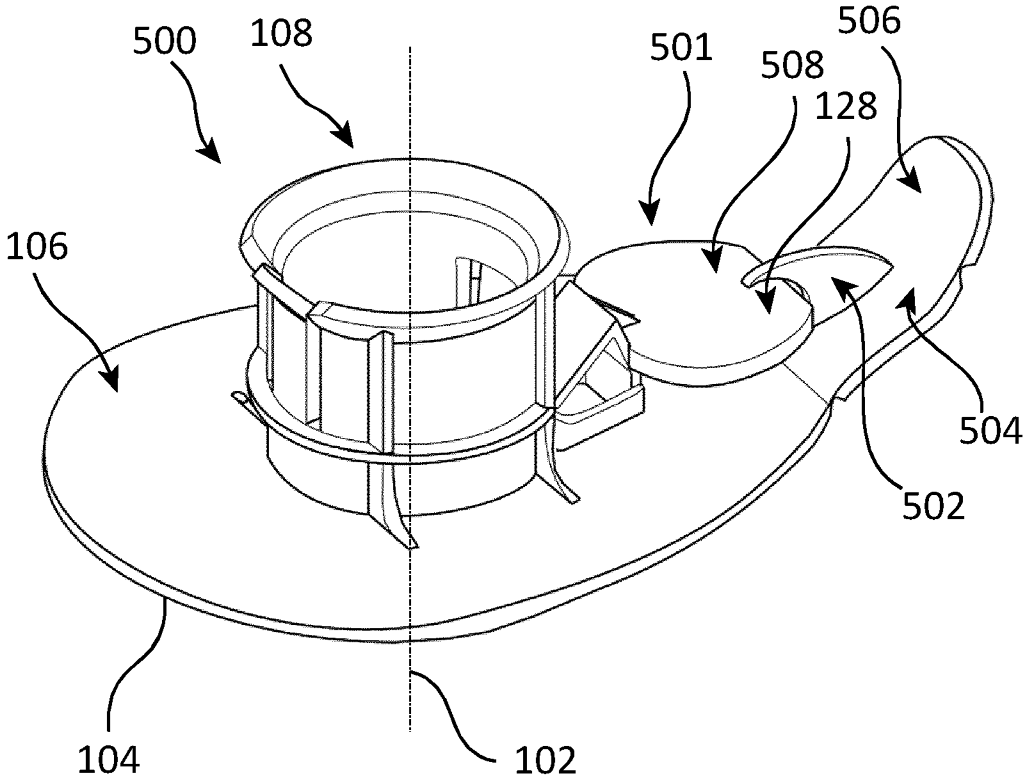
FIG. 16 is a perspective view of a pad according to embodiments of the present disclosure.
Figure 17:
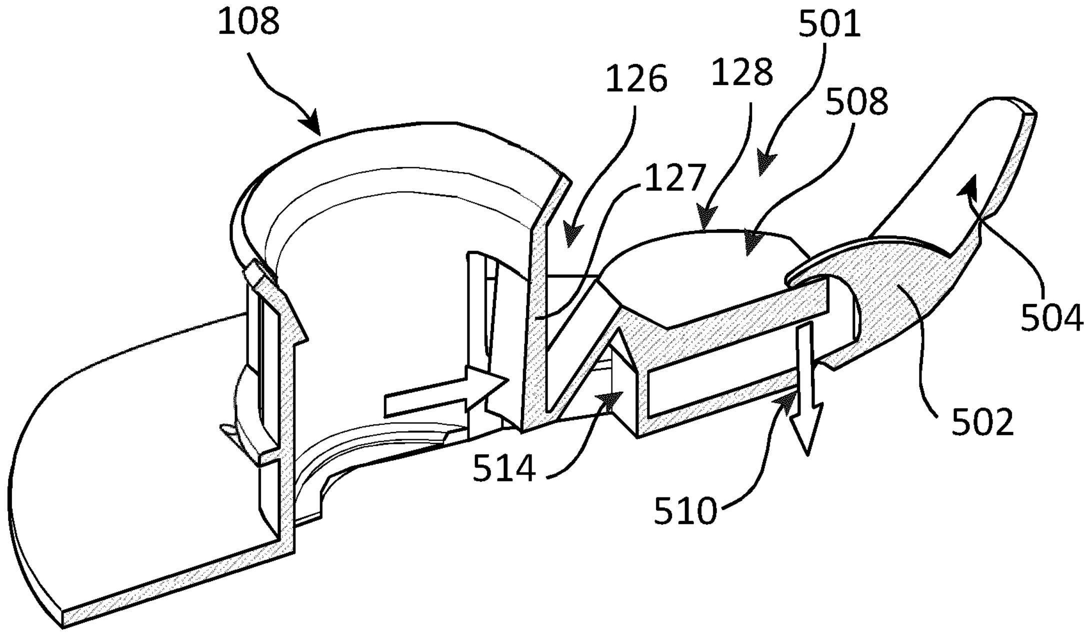
FIG. 17 is a perspective cross-sectional view of the pad in FIG. 16.
Figure 18:
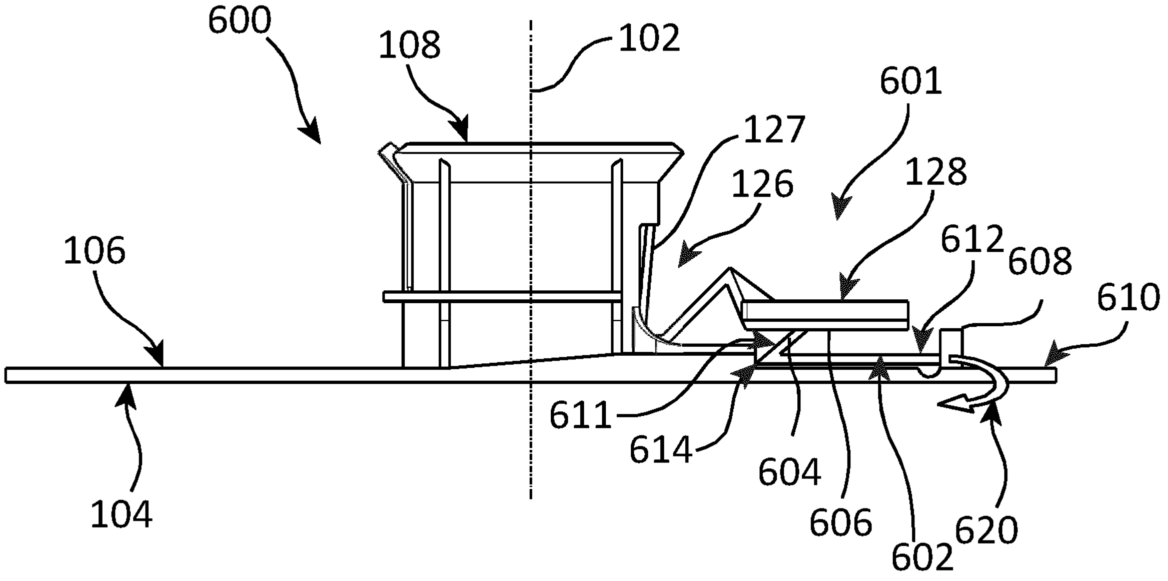
FIG. 18 is a side view of a pad according to embodiments of the present disclosure.

FIGS. 16-18 illustrate pads 500 and 600 according to the second aspect. In this second aspect the pad 500, 600 extends along an axis 102 from a proximal end 104 to a distal end 106. The proximal end 104 is the end of the pad 500, 600 adjacent to an injection site when the pad 500, 600 is in use.

The pad 500, 600 comprises an attachment portion 108 configured to releasably receive a medicament delivery device. The attachment portion comprises a release mechanism 501, 601 which, upon being actuated, releases the medicament delivery device from the pad 500, 600.

The pad 500, 600 comprises a release arm 502, 602 respectively, configured to act on the release mechanism 501, 601 when the pad 500, 600 is being removed from the injection site by transferring a force from the pad caused by the pad being deformed while being removed from the injection site to the release mechanism.

The attachment portion 108 of the pad 500, 600 is equipped with a locking mechanism 126 for releasably locking the medicament delivery device 110 to the pad 100. The locking mechanism 126 comprises a movable arm 127 that applies a holding force on the attachment portion 124 of the medicament delivery device 110, see e.g. FIGS. 2-3. This may be a friction lock.

Turning now to the pad 500 shown in FIGS. 16 and 17, where FIG. 16 is a perspective view and FIG. 17 is a cross-sectional view of the pad 500.

In this embodiment, the release arm 502 is attached to a pad surface 504 at the distal end 106 of the pad 500. The release arm 502 extends, in a distal direction to a distal side of a release button 128 of the release mechanism 126. The release arm 502 is attached to a removing tab 506 of the pad 500 which is adapted to be pulled by the user for removing the pad 500 from the injection site. As the pad 500 is deformed by the user pulling the tab 506, the release arm 502 acts on a distal surface 508 of the release button 128 such that the release mechanism 126 is actuated.

In this embodiment, the release button 128 is attached to the surface at the distal end 106 of the pad 500 via a linkage arm 514.

In use, and when a user pulls the removing tab 506, the hook-shaped release arm 502 reaches to and pushes on the release button 128 in a proximal direction as indicated by arrow 510, towards a surface at the distal end 106 of the pad 500. The movable arm 127 is then pulled in a radial direction of the attachment portion 108 where the medicament delivery device is arranged, see e.g. FIG. 3, whereby the force applied on the medicament delivery device by the movable arm 127 is reduced, thereby releasing the medicament delivery device from the attachment portion 108.

Figure 25:
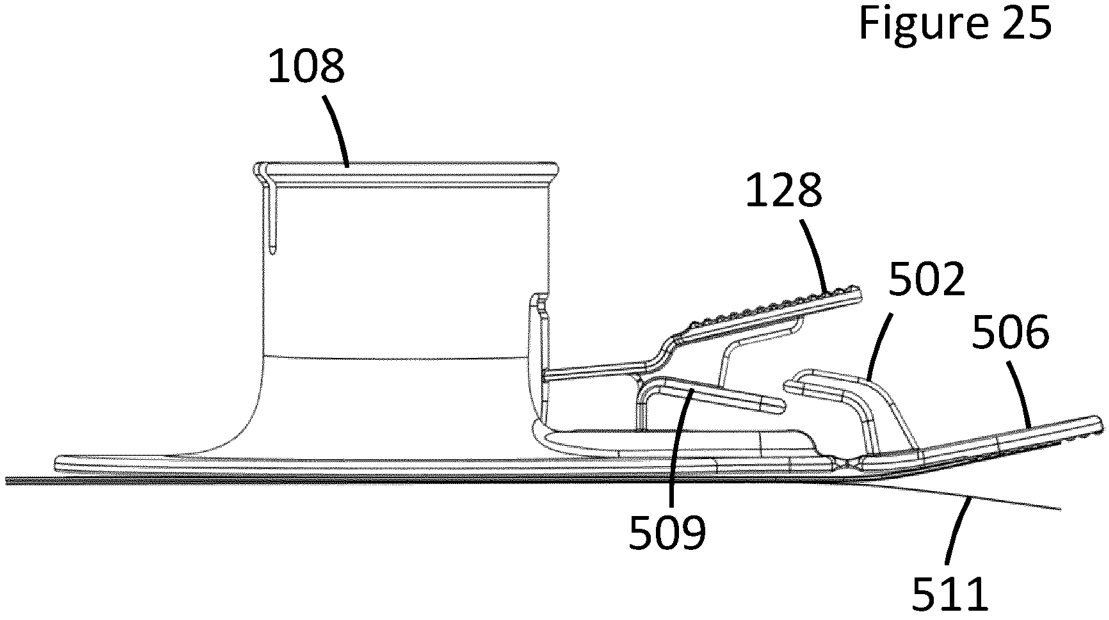

Another pad similar to that in FIGS. 16 and 17 is shown in FIGS. 22 to 25. In this example, the release arm 502 again acts to actuate the release mechanism 126 in the same way as described for the pad in FIGS. 16 and 17, but the release arm 502 acts on a lever 509 rather than directly on the release button 128. As can be seen in FIG. 25 in particular, the lever 509 is attached to the release mechanism 126, including (optionally) to the release button 128. Optional ridging is provided on the distal surface of the release button 128; this can help with grip.

Optional ridging is provided on the proximal surface of the removing tab 506; this can help with grip. Ridging could optionally also be provided elsewhere, such as on the distal surface of the removing tab 506. An optional cover 511 can also be seen; this cover 511 can protect a sticky layer on the proximal end of the pad and would typically be removed by a user before using the pad.

Turning now to FIG. 18 illustrating the pad 600. In this embodiment, a first end 604 of the release arm 602 is attached to a proximal surface 606 of the release button 128. A second end 608 of the release arm 602 is adapted to abut against a distal surface 610 of the pad 600. In this way, when the pad 600 is removed from the injection site, the release arm 602 flexes such that the second end 608 moves in a proximal direction towards the distal end 106 of the pad 600 which causes the release button 128 to be spatially transferred to cause the actuation of the release mechanism 601.

The release arm 602 is adapted to be flexible and biased in the proximal direction and held in place, i.e. to not actuate the release mechanism 126 by the counter force provided by the injection site when the pad 600 is attached to the user.

When the pad 600 is removed, the release arm 602 flexes open and causes a pulling action on the release button 128 in a radial direction so that the movable arm 127 releases the medicament delivery device from the attachment portion 108.

In this specific embodiment, the release arm 602 comprises a first arm portion 611 and a second arm portion 612 forming an acute angle between them. The first arm portion 611 comprises the first end 604 and the second arm portion 612 comprises the second end 608. The joint between the first and second arm portions abuts against a stop edge 614 of the pad 600 to prevent the joint from moving towards the attachment portion 108. When the release arm 602 flexes, the angle between the first arm portion 611 and the second arm portion 612 increases whereby the second arm portion moves along a curved path as indicated by arrow 620, thereby causing the release button 128 to move away from the attachment portion 108 and thereby actuate the release mechanism 601. The flexing motion of the release arm 601 is thus a relative motion between the first arm portion 611 and the second arm portion 612.

The release button 128 of the pad 600 is not attached to the pad distal surface 610, as is the case for the pad 500. The release button 128 of the pad 600 is connected only to the movable arm 127 extending into the attachment portion 108 and to the release arm 602. This advantageously enables for an efficient pulling action on the release button by the release arm 602, when the pad 600 is removed from the injection site.

Figure 19:
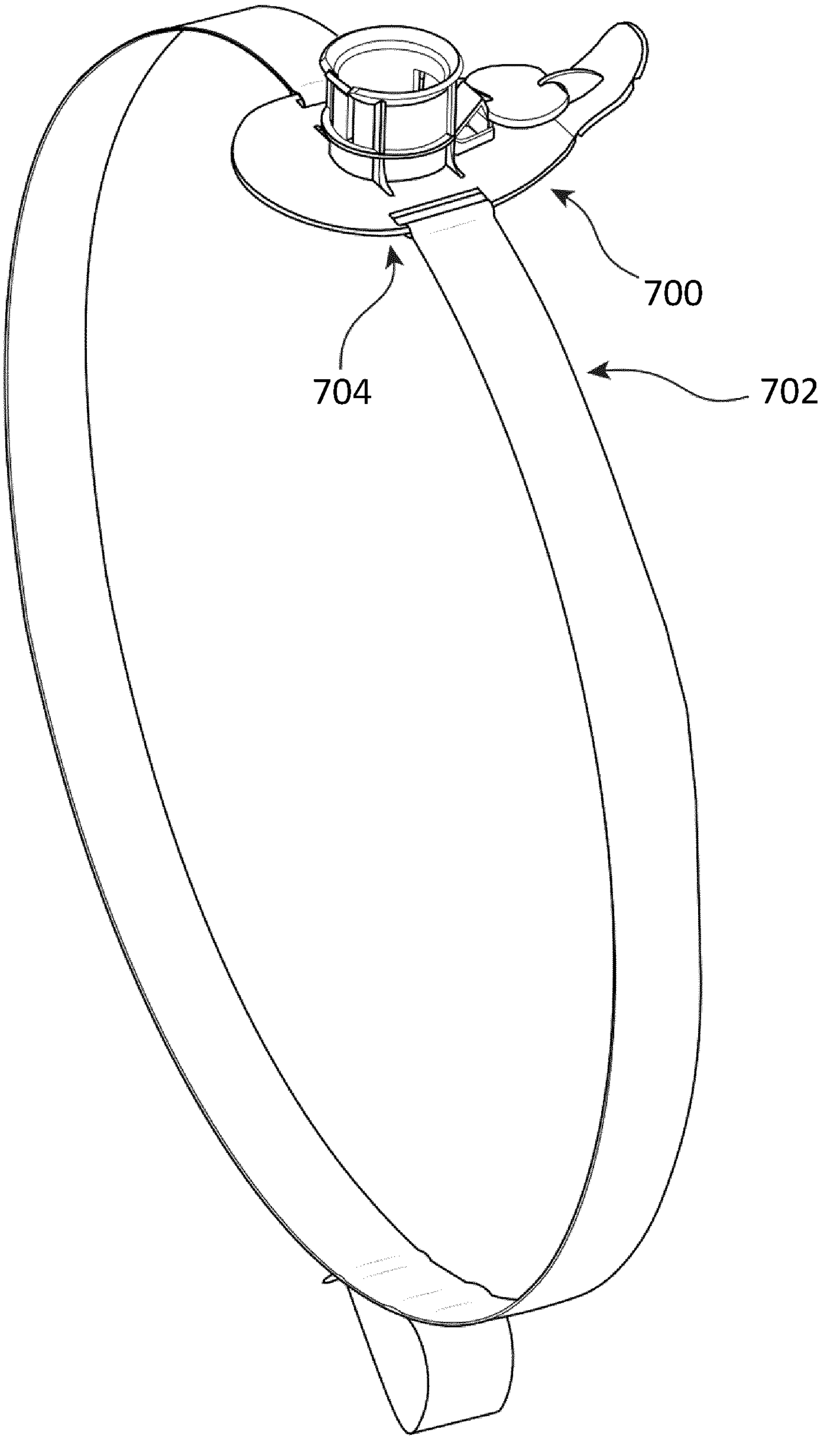
FIG. 19 is a perspective view of a pad with straps according to embodiments of the present disclosure.

FIG. 19 discloses a pad 700 configured to be attached to the injection site via straps 702 instead of adhesive. Straps 702 can be attached via attachment points 704 on the pad 700 or the straps 702 can be directly glued or co-moulded with the pad 700. The straps 702 can be adjusted with locking clips. In possible implementations, Velcro straps can be used for locking the pad 700 on the body.

Figure 20:
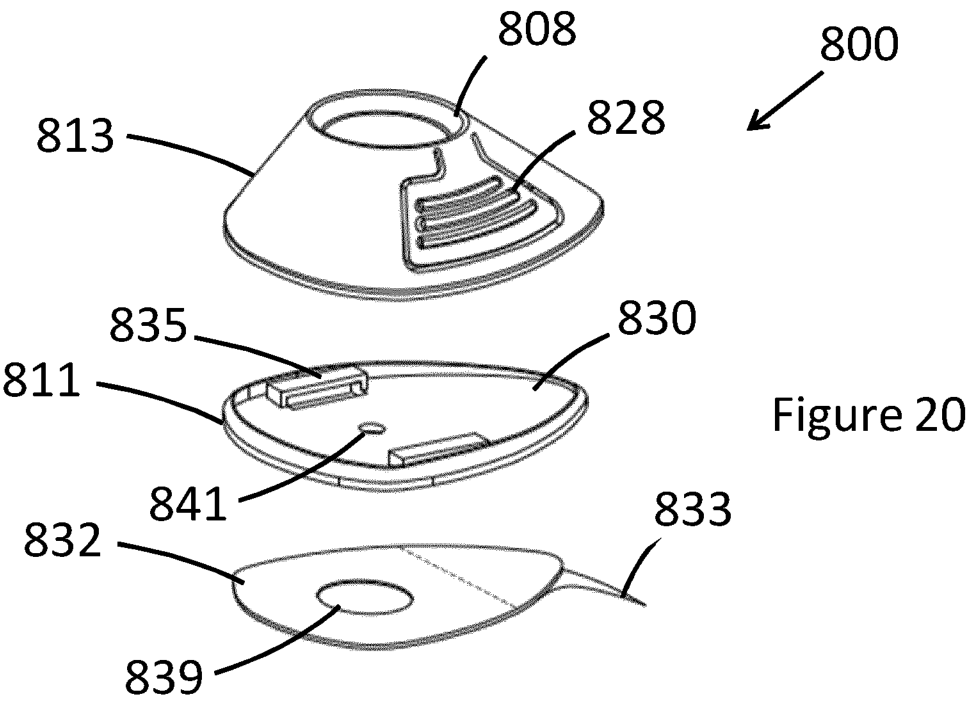
FIGS. 20 and 21 show a pad according to embodiments of the present disclosure.
Figure 21:
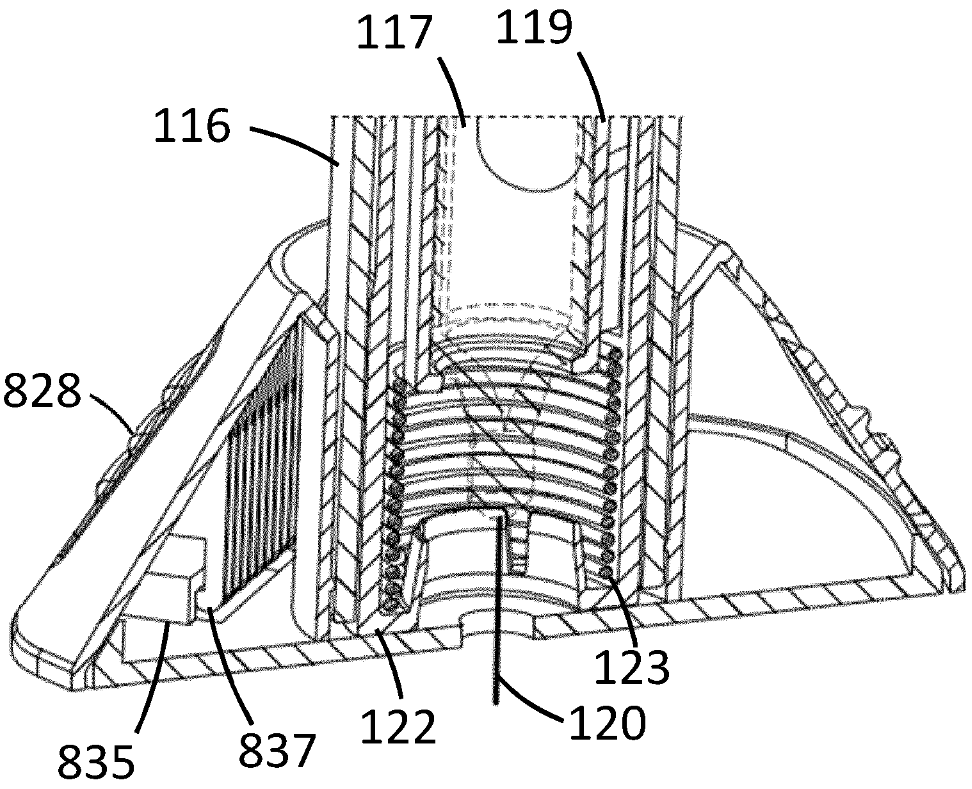
Figure 22:
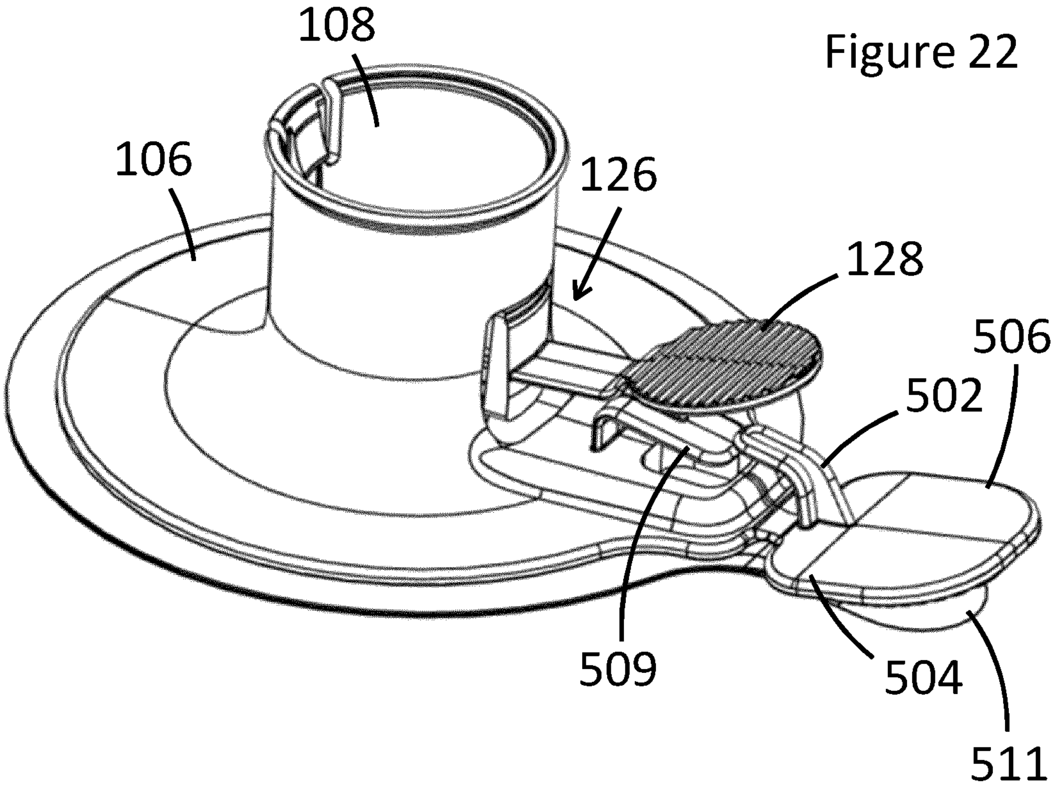
FIGS. 22 to 25 show a pad according to embodiments of the present disclosure.
Figure 23:
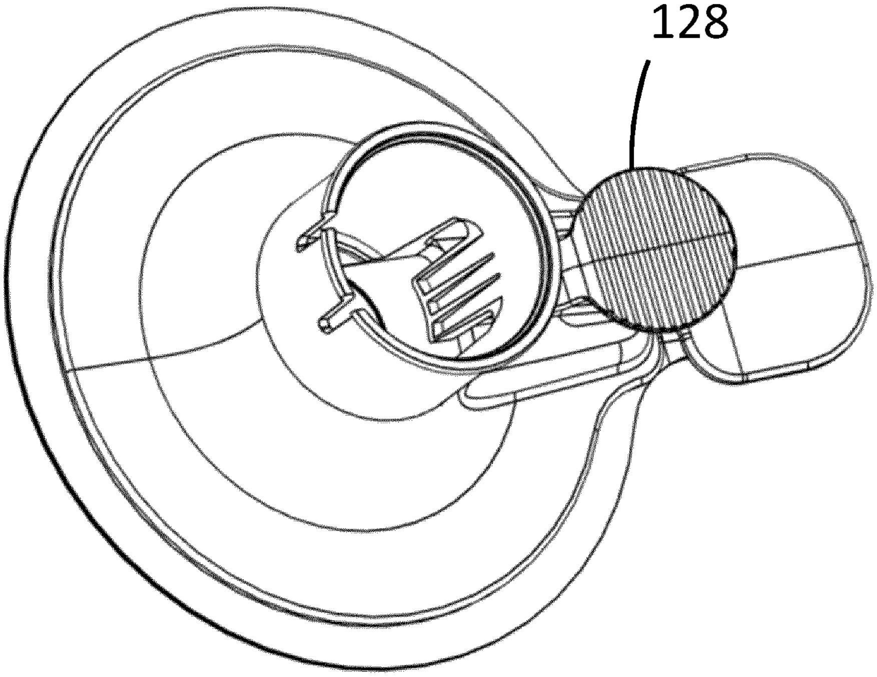
Figure 24:
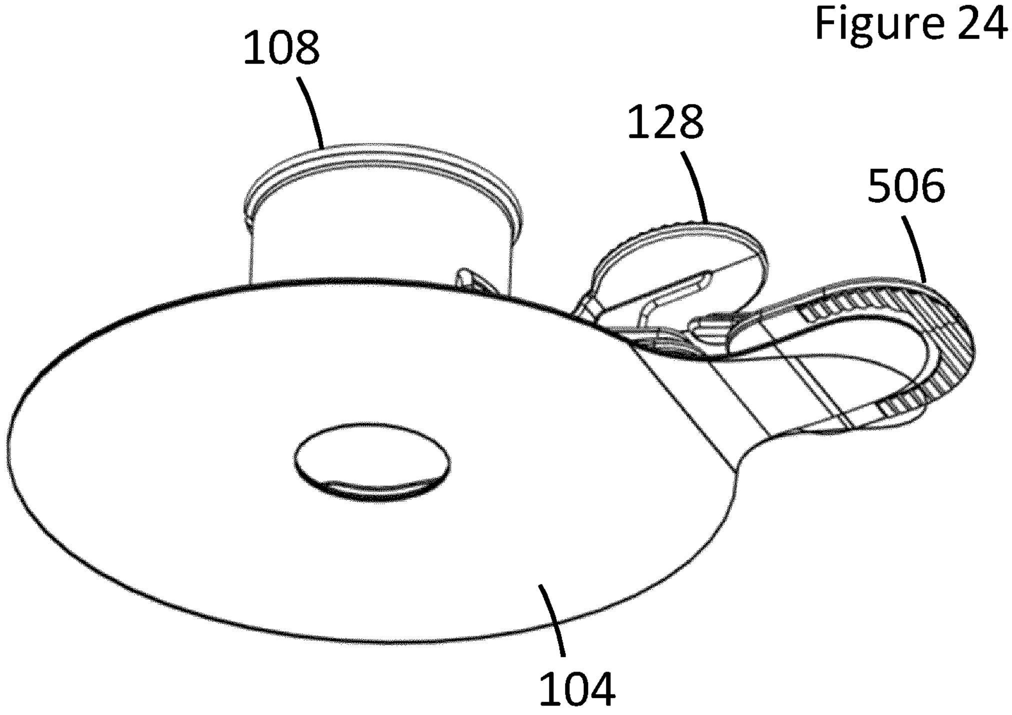

FIGS. 20 and 21 illustrate another pad 800. The pad comprises a proximal part 811 and a distal part 813. The proximal part 811 comprises a proximal injection surface 832 which is shown separately in FIG. 20, and is at the proximal side of the proximal part 811. As with other examples herein, the proximal injection surface 832 is the surface being attached to the injection site via e.g. an adhesive. Thus, the proximal injection surface 832 is adjacent to the injection site when the pad is in use. The proximal injection surface 832 can just be an adhesive layer at the proximal side of the proximal part 811, and can include a removable cover 833 that protects the adhesive layer prior to use. Optionally, the proximal injection surface 832 comprises a hole 839; this can allow the needle to pass through the hole (instead of alternatively piercing the adhesive layer). Similarly, an optional hole 841 in the proximal injection surface 832 can allow the needle to pass through the hole (instead of alternatively piercing the proximal injection surface 832).

The distal part 813 comprises an attachment portion 808. The attachment portion 808 can receive a medicament delivery device such as an autoinjector or pen injector, as shown in FIG. 21 with an autoinjector. In FIG. 21, part of the autoinjector can be seen, comprising a housing 116, a syringe 117 comprising a needle 120, a syringe carrier 119, a cover extension 122 (needle guard), and a cover extension spring 123 of the autoinjector are visible.

The attachment portion 808 comprises an optional tubular section 809. The tubular section can help align a medicament delivery device during insertion into the pad 800.

The frustoconical design of the pad (and the prominent placement of the buttons, which in this example comprise optional ribs to improve the grip of the buttons 828) is designed so that a user will naturally grasp the buttons and thereby release the distal part 813 from the proximal part 811 when trying to remove the medicament delivery device and pad from the injection site after an injection, which can help ensure correct use of the device and the pad even if the user is not strictly following use instructions.

The proximal part 811 is releasably attached to the distal part 813. The distal part 813 comprises a release button 828, which comprises a flexible arm comprising an outwardly extending hook 837 that extends from the flexible arm away from the axis. The proximal part 811 comprises corresponding recesses 835 into which the outwardly extending hooks 837 extend (see FIG. 21). Two release buttons and two corresponding recesses are provided, although alternatively one release button and one corresponding recess is provided.

The proximal part 811 comprises a support structure 830, which in this example is a surface extending perpendicular to the longitudinal axis; the support structure 830 is configured to abut against the medicament delivery device when in use (when the medicament delivery device is arranged in the attachment portion). As can be seen in FIG. 21, this can keep the cover extension in a retracted position.

During use of a pad 800, the pad would typically first be attached to the injection site. A medicament delivery device would be inserted into the pad, and would typically be activated by the insertion into the pad (for example by retracting the cover extension to the position shown in FIG. 21) and/or by a user pressing a button, for example. The medicament delivery device could be held in place relative to the pad (in the position shown in FIG. 21) by a friction fit or a snap fit, for example. This can allow the medicament delivery device to be held in the position shown in FIG. 21 (so in a position where the injection can occur) without a user needing to hold the medicament delivery device in place at the injection site. Once an injection has been completed, a user squeezing the two buttons 828 towards each other releases the hooks 837 from the recesses 835, thereby detaching the proximal part 811 from the distal part 813. As a result, the distal part 813 can be removed from the injection site along with the medicament delivery device, leaving the proximal part 811 attached to the injection site (the proximal part can subsequently be removed from the injection site). Detaching the proximal part 811 from the distal part 813 allows the cover extension 122 to extend from its retracted position (as the proximal part 811 no longer restricts proximal movement of the cover extension 122), thereby covering the needle. In this example, the release of the hooks 837 from the recesses 835 would typically actively push the distal part 813 away from the proximal part 811 due to the cover extension extending.

The pads disclosed herein may be made out of transparent material.

Further, the sidewall of the attachment portion may comprise an opening forming a window close to the base of the attachment portion adjacent the pad surface. Prior to use, instructions may tell the patient to see if the cover extension is fully depressed when using the autoinjector.

With the window and/or the transparent material, the patient is able to inspect the status of the cover extension when using the autoinjector in combination with the injection support pad.

The pads disclosed herein may include embedded electronics which includes different units.

A sensor unit which may recognize injection events, such as the autoinjector inserted into the attachment portion, injection started, and injection ends.

A memory unit which is configured to store the recorded data during the injection.

A connectivity unit configured to transmit the stored data to a smart device or the network directly.

A processing unit configured to control the entire system and process the data before transmitting it.

User interface units that are configured to provide feedback to the patient, such as status LEDs, haptic, and/or audio feedback.

When the auto-injector is placed into the injecting port, the sensors inside of the support pad may be configured to recognize the event and give feedback to the patient via haptic/visual or audio elements.

When the injection finishes, the sensors may be configured to recognize the event and give feedback to the patient again. Further, the collected data is stored in the memory unit and may be transmitted to the smart device/network via the connectivity unit after the injection event finishes.

The sensor can be one of or a combination of the following: a mechanical switch, a Hall-effect sensor, and an accelerometer.

The mechanical switch, hall-effect sensor, and/or accelerometer can be used for detection of the insertion of the auto-injector into the injection port.

The accelerometer can be used for detecting injection events.

Possible wireless communication methods include Bluetooth and Cellular Networks.

Bluetooth connectivity generally requires a smart device to transmit the stored data to the network and it generally requires a pairing action between the support pad and the smart device before being able to use the supporting pad. However, Bluetooth can provide cheaper alternative and it generally requires less space on the PCB (printed circuit board).

Use of a cellular network does not require any pairing process, it can be used as a plug-and-play device, and no prior setup is needed. However, it can be more expensive and it generally requires more space on the PCB.

Depending on the requirements of the product either (or both) of those two technologies can be used.

Such processing units may comprise a logic circuit or control unit including a microprocessor, microcontroller, programmable digital signal processor and/or another programmable device. The processing circuitry may also, or instead, each include an application specific integrated circuit, a programmable gate array or programmable array logic, a programmable logic device, or a digital signal processor. Where the processing circuitry includes a programmable device such as the microprocessor, microcontroller or programmable digital signal processor mentioned above, the processor may further include computer executable code that controls operation of the programmable device.

The presently disclosed concept has mainly been described above with reference to a few examples. However, as is readily appreciated by a person skilled in the art, other embodiments than the ones disclosed above are equally possible within the scope of the presently disclosed concept, as defined by the appended claims.

The invention claimed is:

1. A pad extending along an axis from a proximal end to a distal end, where the proximal end is the end of the pad adjacent to an injection site when the pad is in use, the pad comprising:

an attachment portion configured to releasably receive a medicament delivery device, wherein the attachment portion comprises a release mechanism which, upon being actuated, releases the medicament delivery device from the pad, and a support structure at the proximal end of the attachment portion configured to abut against the medicament delivery device when in use and the medicament delivery device is arranged in the attachment portion, the support structure being configured to be pushed away from the attachment portion by a force exerted by a spring biased cover extension of the medicament delivery device transitioning from a retracted position to an extended position, such that the spring biased cover extension is allowed to move to the extended position in response to the pad being removed from the injection site while the medicament delivery device is present in the attachment portion.

2. The pad according to claim 1, wherein the support structure is at the proximal end of the pad adjacent to the injection site when the pad is in use.

3. The pad according to claim 1, wherein the support structure is configured to allow the cover extension to penetrate through the attachment portion to beyond a plane of the proximal end of the pad.

4. The pad according to claim 1, wherein the support structure comprises at least one flexible arm attached to the pad, the at least one flexible arm being configured to flex by the force from the cover extension.

5. The pad according to claim 1, wherein the support structure comprises a proximal injection surface configured to be separated from the attachment portion by the force exerted by the cover extension.

6. The pad according to claim 5, wherein the proximal injection surface is hinged to a side structure of the pad.

7. The pad according to claim 6, wherein the hinge is a living hinge, wherein the living hinge provides for the support structure including the proximal injection surface to rotate across an axis.

8. The pad according to claim 6, wherein the proximal injection surface comprises a clip configured to hold the proximal injection surface in place prior to release by the force exerted by the cover extension.

9. The pad according to claim 5, wherein the proximal injection surface is adjacent to the injection site when the pad is in use.

10. A pad extending along an axis from a proximal end to a distal end, where the proximal end is the end of the pad adjacent to an injection site when the pad is in use, the pad comprising:

an attachment portion configured to releasably receive a medicament delivery device, wherein the attachment portion comprises a release mechanism which, upon being actuated, releases the medicament delivery device from the pad, and a release arm configured to act on the release mechanism when the pad is being removed from the injection site by transferring a force from the pad caused by the pad being deformed while being removed from the injection site to the release mechanism.

11. The pad according to claim 10, wherein the release arm is attached to a pad surface at the distal end of the pad and extends to a distal surface of a release button of the release mechanism, wherein when the release arm acts on the distal surface of the release button, the release mechanism is actuated.

12. The pad according to claim 11, wherein the release arm acts to push the release button towards a surface of the distal end of the pad.

13. The pad according to claim 11, wherein the release arm is hook shaped to act on the distal surface of the release button.

14. The pad according to claim 11, wherein the release button is attached to the surface at the distal end of the pad via a linkage arm.

15. The pad according to claim 11, wherein the release arm is attached to a removing tab of the pad adapted to be pulled by a user for removing the pad from the injection site.

* * * * *